US008655699B2

(12) United States Patent
Perrin et al.

(10) Patent No.: US 8,655,699 B2
(45) Date of Patent: Feb. 18, 2014

(54) METHOD AND APPARATUS FOR IDENTIFYING PATIENTS OVERDUE FOR AN APPOINTMENT USING STANDARD HEALTHCARE BILLING DATA

(75) Inventors: Brian William Perrin, American Fork, UT (US); Brett Cornell Gerlach, Eagle Mountain, UT (US)

(73) Assignee: Brevium, Inc., Eagle Mountain, UT (US)

( * ) Notice: Subject to any disclaimer, the term of this patent is extended or adjusted under 35 U.S.C. 154(b) by 1010 days.

(21) Appl. No.: 11/938,087

(22) Filed: Nov. 9, 2007

(65) Prior Publication Data

US 2009/0094054 A1 Apr. 9, 2009

Related U.S. Application Data

(63) Continuation of application No. 11/934,615, filed on Nov. 2, 2007, now abandoned, and a continuation of application No. 11/484,340, filed on Jul. 10, 2006, now Pat. No. 8,190,464.

(51) Int. Cl.
G06Q 10/00 (2012.01)
G06Q 50/00 (2012.01)
(52) U.S. Cl.
USPC .................. 705/7.13; 705/2; 705/5; 705/7.12
(58) Field of Classification Search
USPC ......... 705/2, 3, 5, 7.12, 7.13, 7.15, 7.18, 7.19
See application file for complete search history.

(56) References Cited

U.S. PATENT DOCUMENTS 5,065,315 A 11/1991 Garcia
5,483,443 A 1/1996 Milstein et al.
(Continued)

OTHER PUBLICATIONS

Tel-A-Patient . . . the words that work. PowerCalls-DDS Appointment Confirmation System. 1985.*
(Continued)

*Primary Examiner* — Stephanie Delich
(74) *Attorney, Agent, or Firm* — Scheinberg & Associates, PC; John B. Kelly; Michael O. Scheinberg (57) ABSTRACT

A method and apparatus for identifying overdue patients using standard billing or other office management data, so that patients can be contacted and invited to make an appointment. The invention begins by querying the diagnosis codes for each visit from the billing or other encounter tables, and matching these with a set of target medical conditions requiring regular care. Procedure codes and encounter dates for past visits are queried for these patients, to determine when each patient was last seen, and what was done. These procedure codes are matched against a set of exam codes to determine last medical examination dates, and against a set of procedures known to resolve each medical condition. Each condition requiring regular care is matched against any resolving procedures, leaving a set of untreated conditions requiring regular care. Based on the date of the last exam or treatment and accepted standards of care or office policies, a due date is calculated for each patient. The management system is queried for each overdue patient to determine whether they already have an appointment scheduled in the future, or a recall notice recently sent or yet to be sent. Additional filtering based on administrative settings may also be done. Overdue patients requiring contact are then placed on the contact list.

23 Claims, 5 Drawing Sheets

(56) References Cited

U.S. PATENT DOCUMENTS

| | | | |
|---|---|---|---|
| 5,557,514 A | | 9/1996 | Seare et al. |
| 5,737,726 A | | 4/1998 | Cameron et al. |
| 5,748,907 A | | 5/1998 | Crane |
| 5,918,208 A | | 6/1999 | Javitt |
| 5,982,863 A | | 11/1999 | Smiley et al. |
| 6,024,699 A | * | 2/2000 | Surwit et al. ............ 600/300 |
| 6,047,259 A | * | 4/2000 | Campbell et al. ............ 705/3 |
| 6,088,429 A | | 7/2000 | Garcia |
| 6,151,581 A | | 11/2000 | Kraftson et al. |
| 6,393,404 B2 | * | 5/2002 | Waters et al. ............ 705/2 |
| 6,680,999 B1 | | 1/2004 | Garcia |
| 6,988,075 B1 | | 1/2006 | Hacker |
| 7,034,691 B1 | | 4/2006 | Rapaport et al. |
| 7,343,565 B2 | | 3/2008 | Ying et al. |
| 7,436,311 B2 | | 10/2008 | Rapaport et al. |
| 7,702,522 B1 | | 4/2010 | Sholem |
| 7,716,072 B1 | * | 5/2010 | Green et al. ............ 705/3 |
| 7,729,928 B2 | | 6/2010 | Backhaus et al. |
| 7,774,210 B1 | * | 8/2010 | Sandberg ............ 705/2 |
| 7,916,014 B2 | | 3/2011 | Rapaport et al. |
| 7,970,634 B2 | | 6/2011 | Backhaus et al. |
| 8,000,979 B2 | | 8/2011 | Blom |
| 8,000,984 B2 | | 8/2011 | Hasan et al. |
| 8,090,593 B2 | | 1/2012 | Backhaus et al. |
| 2002/0138306 A1 | * | 9/2002 | Sabovich ............ 705/3 |
| 2002/0156672 A1 | * | 10/2002 | Burko ............ 705/9 |
| 2002/0191035 A1 | | 12/2002 | Selent |
| 2003/0120512 A1 | | 6/2003 | Dengler |
| 2003/0195774 A1 | * | 10/2003 | Abbo ............ 705/3 |
| 2004/0019501 A1 | * | 1/2004 | White et al. ............ 705/2 |
| 2004/0181433 A1 | * | 9/2004 | Blair ............ 705/2 |
| 2004/0199406 A1 | | 10/2004 | Owens et al. |
| 2004/0243436 A1 | | 12/2004 | Rawat et al. |
| 2005/0234739 A1 | | 10/2005 | Schoenberg |
| 2006/0047552 A1 | * | 3/2006 | Larsen et al. ............ 705/8 |
| 2006/0047553 A1 | | 3/2006 | Fuhrmann et al. |
| 2006/0047554 A1 | | 3/2006 | Larsen et al. |
| 2006/0053044 A1 | * | 3/2006 | Kurian et al. ............ 705/9 |
| 2006/0116911 A1 | * | 6/2006 | Tremblay et al. ............ 705/4 |
| 2007/0078697 A1 | | 4/2007 | Nixon |
| 2008/0306781 A1 | | 12/2008 | Gerlach et al. |
| 2009/0055220 A1 | | 2/2009 | Rapaport et al. |
| 2009/0161846 A1 | | 6/2009 | Perrin et al. |

OTHER PUBLICATIONS

Vaccine Reminder Recall System: A Practical Guide for Pediatric Practices. American Academy of Pediatrics. Jun. 1984, Timeline for Implementation. Aug. 1989 Complete Electronic Medical Record.*

Elexity.com; 2004-2007; Elexity; retrieved Jun. 9, 2009 [www.elexity.com; http://web.archive.org/web/20070920075315/www.elexity.com/generalSite/solutionsApptReminders.asp].

Phytel.com; 2004; Phytel; retrieved Jun. 9, 2009 [www.phytel.com; http://web.archive.org/web/20041021033228/phytel.com/solutions/appointmentconfirmations.html].

Smilereminder.Com, Webpages, 2002, Retrieved Sep. 17, 2009, [http://web.archive.org/web/20021210135102/www.smilereminder.com/index.html], 3 Pages.

Phytel.Com, Brochure, 2002, Exact publication date unknown, Retrieved Sep. 17, 2009, [http://web.archive.org/web/20030407162143/phytel.com/brochure.pdf], 6 Pages.

Phytel.Com, Webpages, 2006, Exact publication date unknown, Retrieved Sep. 17, 2009, [http://web.archive.org/web/20060813164142/http://www.phytel.com], 4 Pages.

Phytel.Com, Webpages, 2007, Exact publication date unknown, Retrieved Sep. 17, 2009, [http://web.archive.org/web/20071024121500/www.phytel.com/products/products01.htm], 3 Pages.

Corey, David J., "Appointment Standardization Integrated Program Team Meeting—Activation of MCP Status." Department of Defense-Tricare Management Activity, Oct. 24, 2000, 22 Pages.

Health Systems Management Group, "Medical Practice Expert Software Features," Webpages, 2005, Exact publication date unknown, Retrieved Apr. 26, 2010, [http"//web.archive.org/web/20050324141543/www.hsmg.biz/cal.med/features/html/], 9 Pages.

CPM Marketing Group, Inc., "Life Connections," Webpages, 2006, Exact publication date unknown, Retrieved Apr. 26, 2010, [http://web.archive.org/web/20060308193454/www.cpm.com/physicians/solutions/corecomm.cfm], 8 Pages.

Frieden,Joyce, "Electronic Health Records Yield Business Payoff," Internal Medicine News, Jan. 15, 2006, p. 76, vol. 39, No. 2, p. 76, ISSN 1097-8690, pp. 10-11.

Adams, Vicki J., et al., Analysis of Practice Management Computer Software Program for Owner Compliance with Recall Reminders, Can Vet J, 2006, pp. 234-240, vol. 47.

11484340-381857 EICSEARCH, 55 pages, Jan. 4, 2012.

Hashim, Muhammad Jawad, et al., 'Effectiveness of Telephone Reminders in Improving Rate of Appointments Kept at an Outpatient Clinic: A Randomized Controlled Trial,' Department of Family Medicine, University of Rochester New York, Mar. 14, 2011, 4 pages.

O'Hare, C. Dennis, et al., 'The Outcomes of Open-Access Scheduling,' Family Practice Management, Feb. 2004, 8 pages.

Venkataramu, Raghunandan Yedehalli, 'A Revenue Management Framework for Appointment Allocation in Rehabilitation Outpatient Clinics,' 2005, 73 pages.

Mohr, Angie, 'Statistics can point you in the direction of profitability,' The Record, May 4, 2005, 2 pages.

* cited by examiner

| diag_id | description | code | is_resolve | is-icd9 | visit_Interval |
|---|---|---|---|---|---|
| 19 | Borderline Glaucoma | 365.[^0135]% | 1 | 1 | 12 |
| 16 | Borderline Glaucoma | 365.[03]% | 0 | 1 | 12 |
| 18 | Borderline Glaucoma | 365.[15][^2] | 1 | 1 | 12 |
| 17 | Borderline Glaucoma | 365.[15]2 | 0 | 1 | 12 |
| 1 | Cataracts | 366.[^5]% | 0 | 1 | 6 |
| 2 | Cataracts | 366.5% | 1 | 1 | 6 |
| 5 | Cataracts | 6698[24] | 1 | 0 | 6 |
| 3 | Cataracts | V27.88 | 1 | 1 | 6 |
| 4 | Cataracts | V43.1% | 1 | 1 | 6 |
| 6 | Diabetes | 250% | 0 | 1 | 12 |
| 7 | Diabetes | 362.0% | 0 | 1 | 12 |
| 8 | Routine Exam | 367.[01] | 0 | 1 | 24 |
| 9 | Routine Exam | 367.2[01] | 0 | 1 | 24 |
| 10 | Routine Exam | 367.4 | 0 | 1 | 24 |
| 11 | Routine Exam | 367.89 | 0 | 1 | 24 |
| 12 | Routine Exam | V72.0 | 0 | 1 | 24 |
| 22 | Glaucoma | 365.[^0135]% | 0 | 1 | 4 |
| 21 | Glaucoma | 365.[15][^2] | 0 | 1 | 4 |
| 14 | Macular Degeneration | 362.5% | 0 | 1 | 6 |

FIG. 3

| exam_codes |
|---|
| 92002 |
| 92004 |
| 92012 |
| 92014 |
| 99201 |
| 99202 |
| 99203 |
| 99204 |
| 99205 |
| 99212 |
| 99213 |
| 99214 |
| 99215 |

METHOD AND APPARATUS FOR IDENTIFYING PATIENTS OVERDUE FOR AN APPOINTMENT USING STANDARD HEALTHCARE BILLING DATA

This application claims priority from U.S. patent application Ser. No. 11/484,340, filed Jul. 10, 2006 for "Method and Apparatus for Identifying and Contacting Customers Who are Due for a Visit but have not Scheduled an Appointment," and from U.S. patent application Ser. No. 11/934,615, filed Nov. 2, 2007 for "Method and Apparatus for Identifying Patients Overdue for an Appointment Using Standard Healthcare Billing Data," both of which are hereby incorporated by reference.

TECHNICAL FIELD OF THE INVENTION

The present invention relates to a method and apparatus for internal marketing, and more particularly, to a method and apparatus for identifying patients who are due for a health care appointment and facilitating contact with those patients.

BACKGROUND AND SUMMARY OF THE INVENTION

Most healthcare practices rely on scheduled appointments to provide an agreed time and place to serve patients. In many cases, after serving a patient, a return appointment will be recommended for some time in the future. Often, an appointment is made for a return visit before the patient leaves the office. However, if the needed appointment is too far out, if staff schedules are unreliable, or if a suitable appointment cannot be found quickly, then the office may instead choose to use a recall. A recall is a notice, sent to the patient prior to the desired appointment date, reminding the patient to call to schedule an appointment.

Contacting patients who are overdue for health care services is a cost-effective way of both improving care and increasing revenue by filling available appointments. However, existing methods of identifying overdue patients use unreliable means of identifying patients who are overdue for care. Consequently, the call list is often both incomplete and inaccurate.

Many management systems that schedule patient appointments provide support for recall notices. Typically, these systems allow entry of a target date for the unscheduled appointment, which is associated with the patient, and some notes about the reason for the recall. On a regular basis, the management system is used to generate printed cards, letters or address labels, so that reminders to call for an appointment can be sent to the appropriate patients. Instead of printed reminders, automated calling systems are sometimes used to leave a recorded message requesting a return call to schedule an appointment.

These systems often provide a list of patients who have not responded to recall notices, so that these patients can be contacted or reminded again. Unfortunately, a simple list of unresponsive patients is inadequate for multiple schedulers involved in a shared, sustained effort to contact patients and schedule these appointments. Schedulers require a record of the times and dates of messages left so that additional messages are not left with the same patients until a sufficient time has elapsed as to warrant another contact. Further, schedulers require that as patients are contacted successfully and appointments are scheduled, that these patients are deleted from the list so that these are not contacted again after an appointment is made.

Thus, the health care industry needs a system for generating complete and reliable call lists using only data that is readily available in most offices.

SUMMARY OF THE INVENTION

An object of the present invention is to use health care data from a database to identify patients who require appointments for health care and to facilitate contacting such patients to schedule appointments.

The present invention improves internal marketing by recapturing lost business by identifying and facilitating the contacting of patients who have not scheduled an appointment.

In a typical embodiment, a system uses information about a health condition, for example, from medical or dental billing data in a practice management system, to determine when a patient appointment is required. The system then facilitates contact with the patient to schedule the appointment.

DETAILED DESCRIPTION OF THE PREFERRED EMBODIMENT

One aspect of some embodiments of the invention is the identification of patients who are overdue for care without having to rely on recall data, appointment types or notes, or electronic medical records.

Another aspect of some embodiments of the invention is the identification of patients' health conditions more specifically, so that required visit intervals can be determined more accurately when no recall data exists.

Another aspect of some embodiments of the invention is the recognition of patients who have been cured of specific medical or dental conditions, so that their required visit intervals can be appropriately updated or eliminated.

Some embodiments of the present invention overcome the limitations of the prior art by using standard diagnosis and procedure codes available in billing or other encounter tables to identify patients with specific conditions, in order to accurately identify patients who are overdue for care. In addition, using these codes enables the current system to identify conditions which have been resolved and no longer require regular care. The benefits are a far more complete and accurate list of patients requiring contact. The codes, such as billing codes and procedural codes are typically available in a one or more practice databases used in a typical health care practice. The scheduling software, billing software, and associated databases are referred to as a "practice management system." Software of the present invention can be used together with an existing practice management system, or can be integrated into a practice management system. The term "electronic medical records" typically connotes a different type of software from practice management software, although the two may be integrated. Electronic medical records typically replace the patients' medical charts and include the patient's subjective complaint, the objective examination results, the clinician's assessment and a care plan. Embodiments of the invention do not require electronic medical records, which are not as ubiquitous as practice management software.

Figure 1:
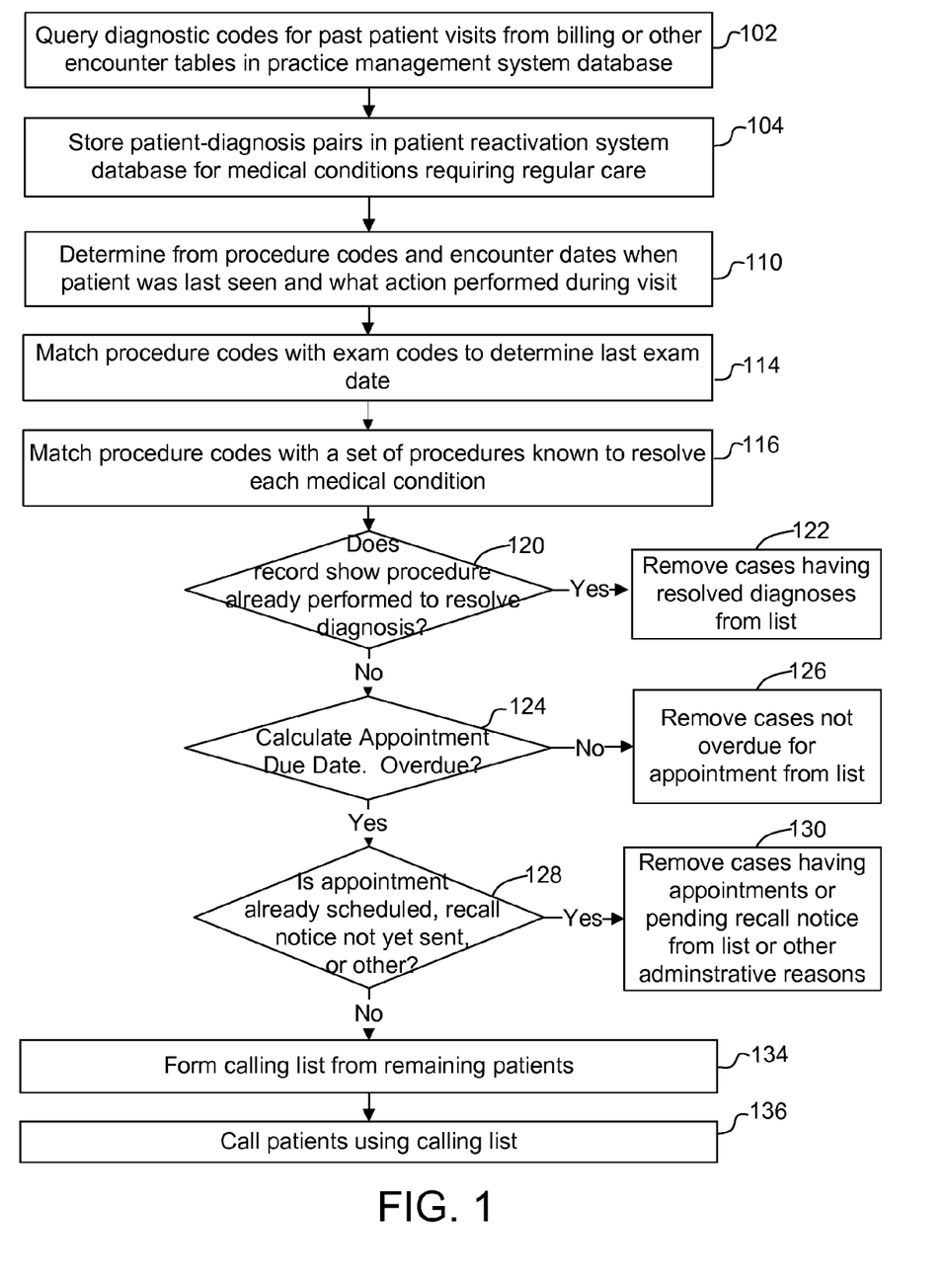
FIG. 1 is a flow chart showing a preferred method in accordance with the invention.

FIG. 1 shows the steps of a preferred embodiment. In step 102, the system queries the diagnosis codes for past patient visits from the billing or other encounter tables in the practice management system. In step 104, the system matches these codes with a set of target conditions requiring regular care and, if a patient's diagnostic code indicates that he requires regular care, the patient's identification, along with the corresponding diagnosis, is stored as patient-diagnosis pairs in a patient reactivation system.

Next, in step 110, the procedure codes and encounter dates for past visits are queried for the patients stored in the patient reactivation system to determine when each patient was last seen, and what was done. In step 114, these procedure codes are matched against a set of exam codes to determine the dates of the last examination. In step 116, the procedure codes are matched against a set of procedures known to resolve each medical condition.

In decision block 120, each condition requiring regular care is matched against any resolving procedures and in step 122, cases in which the diagnosis has been resolved are eliminated from the list, leaving a set of untreated conditions requiring regular care. Based on the date of the last exam or treatment and accepted standards of care or office policies, a due date is calculated for each patient as part of decision block step 124. Patients that are not overdue for making an appointment in accordance with predetermined standards are eliminated from the list in step 126.

In step 128, the system checks each patient on the list to determine whether they already have an appointment scheduled or a pending recall notice yet to be sent, and if so, those patients are removed from the follow-up list in step 130. Patients may also be removed from the list for other, miscellaneous administrative reasons, as described below. Overdue patients without an appointment or pending recall notice form a contact list in step 134 and are contacted, either by a person or by an automatic messaging machine, in step 136.

In summary, the steps of a preferred method can be broadly described as: Query the management system for a list of all patients who have diagnoses requiring regular treatment, and store these as patient-diagnosis pairs in the patient reactivation system. Eliminate patient-diagnosis pairs where the diagnosis has been resolved. Determine the date of the most recent treatment for unresolved diagnoses. Identify patients who are overdue for care. Eliminate from the list patients who already have appointments. Eliminate from the list patients who recently received or who will receive reminders to call for an appointment. Eliminate from the list patients excluded as per administrative settings. These steps are described in more detail below. The steps described above are preferably performed automatically under computer control. That is, the steps are performed by the computer in accordance with programmed instructions and without human intervention. Automatic operation does not exclude a person initiating any step or the entire process.

Query the Management System for a List of all Patients Who have Diagnoses Requiring Regular Treatment, and Store these as Patient-Diagnoses Pairs.

The diagnosis code table 202 (FIG. 2) is part of the preferred patient reactivation system 200, and provides a list of diagnoses which require regular care. This table is interpreted as follows (see FIG. 3). Codes in rows where is_resolve=0 indicate the diagnosis of the given medical condition. Codes in rows where is_resolve=1 indicate resolution (cure) of the given condition. When is_icd9=1, it indicates the code is a diagnosis code (for example, an ICD9-CM code). When is_icd9=0, it indicates the code is a procedure code (for example, a CPT-4 code). The codes in this table are Transact-SQL search strings. Visit_interval gives the number of months between visits, according to accepted standards of care or office policies. Description provides a human-readable description of each medical condition.

If a management system has been used by the practice to bill Medicare or other insurance companies, then standard diagnosis codes and procedure codes will be recorded in tables associated with these patient charges, along with the dates of encounters, rendering providers and locations. There are many different management systems, each with its own database schema, so the exact query will vary from system to system. However, most of these systems are built on standard database products, such as Microsoft SQL Server, which can be queried using standard, documented query language.

Figure 2:
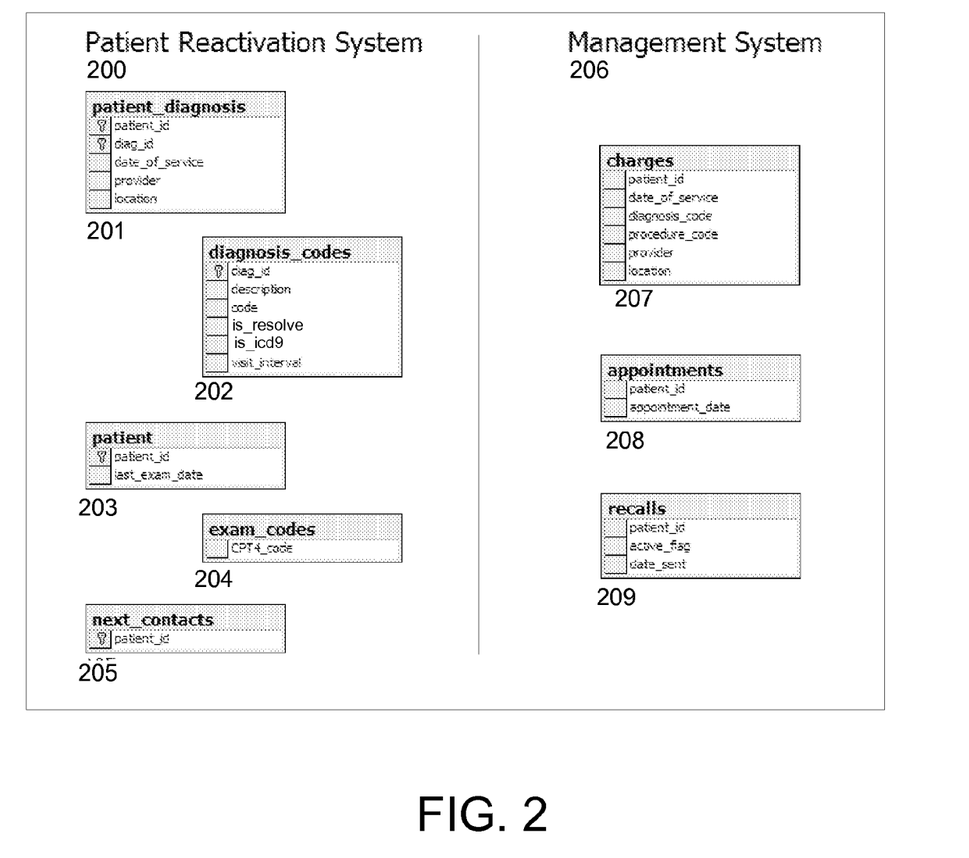
FIG. 2 is a diagram of portions of tables relevant to the present invention, in the management system and in the patient reactivation system described in this invention.

Query the management system 206 for charges 207 whose diagnosis codes match the Transact-SQL search strings in the diagnosis code table 202 where is_resolve=0, and store into the patient_diagnosis table 201 the patient_id, diag_id, date_of_service, provider and location for each matching charge. When there are duplicate diagnoses for the same patient, store only the most recent. For example, if a patient is diagnosed in Mar. 6, 2007 for glaucoma, and returns in Aug. 11, 2007 and is again diagnosed with glaucoma, and in addition is diagnosed with cataracts, store one glaucoma diagnosis for this patient with a date of Aug. 11, 2007, and a cataract diagnosis for this patient with the same date. Do not store the Mar. 6, 2007 glaucoma diagnosis.

Eliminate Patient-Diagnosis Pairs where the Diagnosis has been Resolved.

Figure 3:
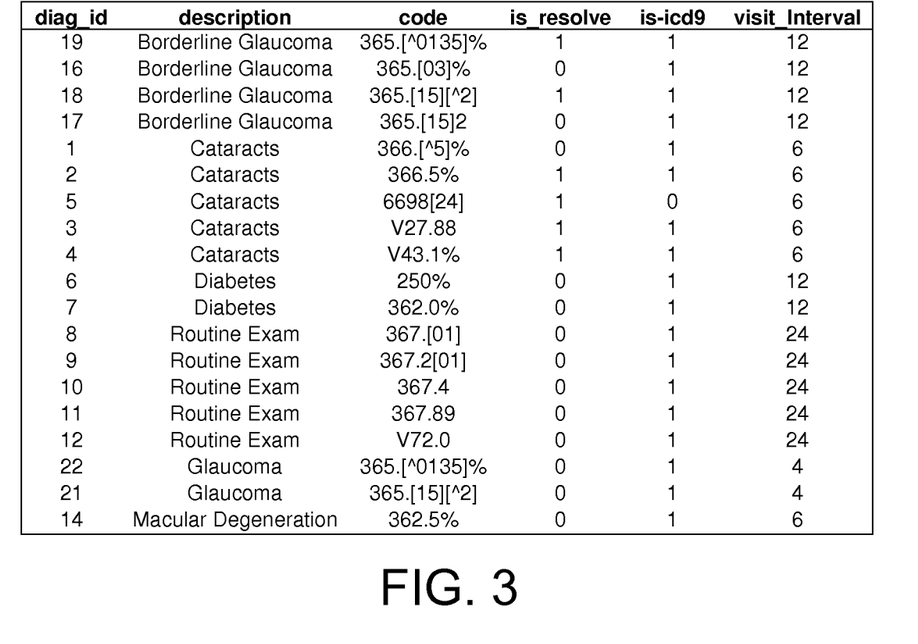
FIG. 3 is an exemplary table of Transact-SQL search strings that will match standard diagnosis codes used to identify conditions requiring regular care, and resolution of these conditions. This table also indicates the normal visit interval for each condition.

Query the management system 206 for charges 207 whose diagnosis or procedure codes match the Transact-SQL search strings in the diagnosis code table 202 where is_resolve=1 (FIG. 3). Delete from the patient_diagnosis table (201) any rows with a matching diag_id, where the date of diagnosis is earlier than or equal to the date of resolution.

Determine the Date of the Most Recent Treatment for Unresolved Conditions.

This step differentiates between visits that are related to the unresolved diagnosis and visits for other purposes that should not affect the due date. Regularly scheduled exams are often used to follow medical conditions which must be monitored closely. Other procedures may also provide regular treatment. If the management system is used to bill Medicare or commercial insurance companies, then any medical services provided will be identified with the charges using standard procedure codes, such as CPT-4 codes. The date of service, rendering provider, location and patient id will also be recorded in these tables.

Figure 4:
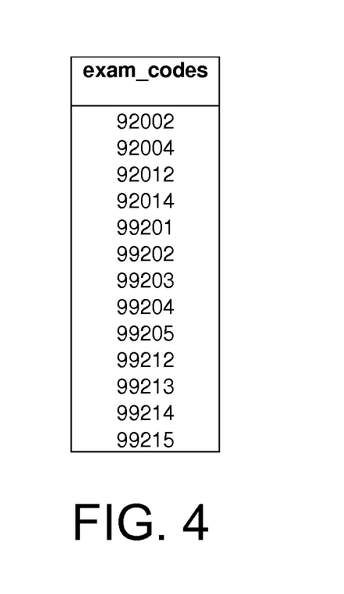
FIG. 4 is an exemplary table of standard procedure codes indicating ophthalmology exams. When matched with specific encounters in the billing tables, these indicate the dates of past examinations.

FIG. 4 shows an exemplary table of exam codes for ophthalmology. The procedures represented by these codes are used to treat the conditions listed in FIG. 3, but do not cure these conditions.

To determine the date of the most recent treatment for unresolved conditions, query the management system's billing or encounter tables for charges 207 whose procedure codes match any of the codes in the table of exam codes 204. For each patient, store the most recent date of a matching encounter as the last_exam date in the patient table 203.

Identify Patients Who are Overdue for Care.

Join the patient_diagnosis table 201 to the diagnosis_code table 202 on the diag_id field and to the patient table 203 on the patient_id field. For each row in the resulting table, calculate the time since the last examination and compare it to the visit interval for the given diagnosis. If the time since last examination exceeds the visit interval, then the patient is overdue. Store the list of patient_id's for patients who are overdue into the next_contacts table 205.

Eliminate from the List Patients Who Already have Appointments

Query the management system 206 for appointments 208 in the future for each patient in the next contacts list. Delete any patients from the next_contacts table 205 who have future appointments scheduled.

Eliminate from the List Patients Who Recently Received or Who Will Receive Reminders to Call for an Appointment.

Query the management system 206 for recalls 209 which will be sent in the future, or which have been sent recently (for example, within six weeks), and delete any patients from the next_contacts table 205 who have just been sent or who will receive recall notices.

Eliminate from the List Patients Excluded as Per Administrative Settings.

Various other administrative settings may indicate patients who should not be contacted, such as patients having specific insurance, patients within a given age range, patients who have not been seen for a very long time, patients seen by specific doctors or at specific locations, patients who have been discharged or are in collections, deceased patients, and so on. These checks are made using additional queries, and matching patients are deleted from the next_contacts table 205.

Telephone the Patient

Figure 5:
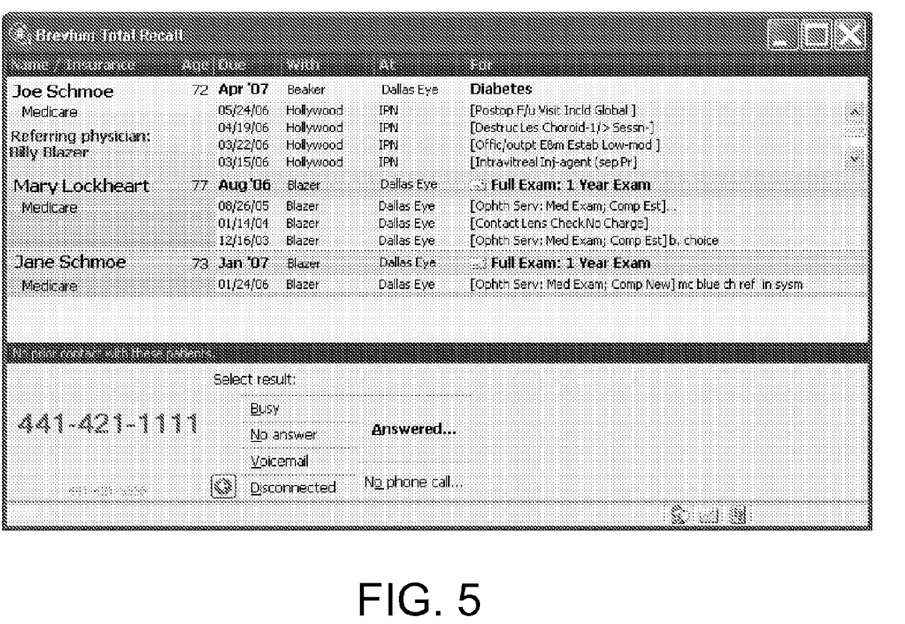
FIG. 5 shows a display screen used to provide into to and collect information from a caller.

In step 138, information about the patient is displayed for a human caller to telephone the patient. FIG. 5 shows a typical display screen. The information preferably includes the patient's name, telephone number, and the reason that an appointment should be made. The caller reviews the information and telephones the patient. The actual dialing may be performed by an automatic dialing system. Alternatively, an automatic messaging system can call the patient and leave a message.

Enter Call Result Information

The caller enters the call results into the lower portion of the screen shown in FIG. 5. The caller may also schedule an appointment for the patient while the patient is on the telephone. In some embodiments, the caller may transfer the patient to a scheduler to schedule the appointment. The caller preferably works in the same office that will provide care for the patient to facilitate scheduling and to increase the likelihood that the caller is personally known to the patient.

FIG. 5 shows several possible call results, including "busy," "no answer," "voice mail," and "disconnected," that the caller may enter. If the patient answered the call, the caller follows the link "answered," which leads to other choices (not shown), such as "appointment made," "condition resolved," "call back at specified time," "call a different number," that the caller may select. The system can then determine from the entered call results whether or not a subsequent call is required and can determine the optimum time for any subsequent call back. The system may determine from the entry that no call back is required, and the patient can be removed from the contact list. If an automatic calling system was used, the call result information may be limited to "no answer", "busy" and "left message."

While an automated dialing machine can be used to dial the patient's number, it is preferable to have a real person speak to the patient, rather than having a machine deliver a recorded or computer generated message. An automated machine leaving a message provides one way communication; it does not provide two way communications in which the patient can respond, ask questions, or have any interaction.

Having a real person speak to the patient provides several benefits. The primary purpose of contacting the patient, that is, the scheduling of an appointment, can be more readily accomplished if the patient can schedule an appointment during the call. A recorded message can only prompt the patient to call the office to schedule an appointment, and some patients may not have sufficient motivation to call the office back. Moreover, patients typically appreciate a personal contact, rather than an impersonal, canned message. The healthcare office staff will often know the patient, and a patient is more likely make an appointment when speaking to a person with whom he has a relationship. Unlike an automated dialing machine, a person can answer the patient's question and address a patient's concerns.

Some types of calls, such as LASIK scheduling, require expertise on the part of the caller. It is undesirable to leave an impersonal, prerecorded message for a candidate for LASIK surgery. These patients want to know that the medical staff is going to provide attentive personal care, and a personal telephone contact can reassure them. Such patients will often have additional medical concerns that will need to be resolved, may have questions about financing, or may have other issues to be addressed by the caller. Some patients may not be ready to schedule an appointment, but they may be ready to take a small step forward in terms of resolving concerns, and a human can help them to advance in this way—a canned message cannot.

A person making the call can collect information that is useful in determining the patient's progress toward resolution. Automated systems are unable to sensitively and accurately collect the rich result information that can be collected by a human caller, such as whether a patient has died or has lost insurance, which would indicate that a patient should not be called back, and so patients and members of their families may continue to be bothered by unnecessary messages, and the office contact system will not be purged of futile contacts. Other family members may provide this information to a human caller, but are less likely to call back to provide this information after receiving a canned message. Repeated reminder calls to a deceased patient's household may be upsetting to the family. One solution to avoid creating ill will with automated system is to limit the number of messages left, but this will reduce the number of patients that are reactivated. In addition, automated systems will not recognize situations where a patient is deliberately refusing needed care. A human caller can report this information and thereby alert the practice that it may want to send a letter of noncompliance or discharge the patient, etc. in order to avoid unnecessary liability. Thus, automated systems are not well suited to tracking patients to resolution. Automated systems tend to be used to make a set number of calls or messages, and quit, without getting a clear answer about what has happened with that patient.

The rich information received from a human caller allows for more appropriate spacing of calls. For example, if the person answering the phone is not the patient, a human caller can record a preferred callback time, a different call back number, or an indication that the patient prefers to call the office back. A human caller can also record if the patient does not want to be called at all. With an automated calling system, calls may be too frequent or the system may stop calling too soon.

Also, a call record recorded by a person provides a more credible, verifiable record of the contact in the event it ever becomes necessary to prove that a call was made and what was said.

Thus, by displaying a screen that provides a human operator with the number to call to reach the patient, information about the caller, and fields in which to record the results of the call, embodiments of the present invention that use human callers provide advantages, not only in determining which patients to call, but also in increasing the number of appointments made and overall patient satisfaction with the health care organization.

Hardware Schematic

Figure 6:
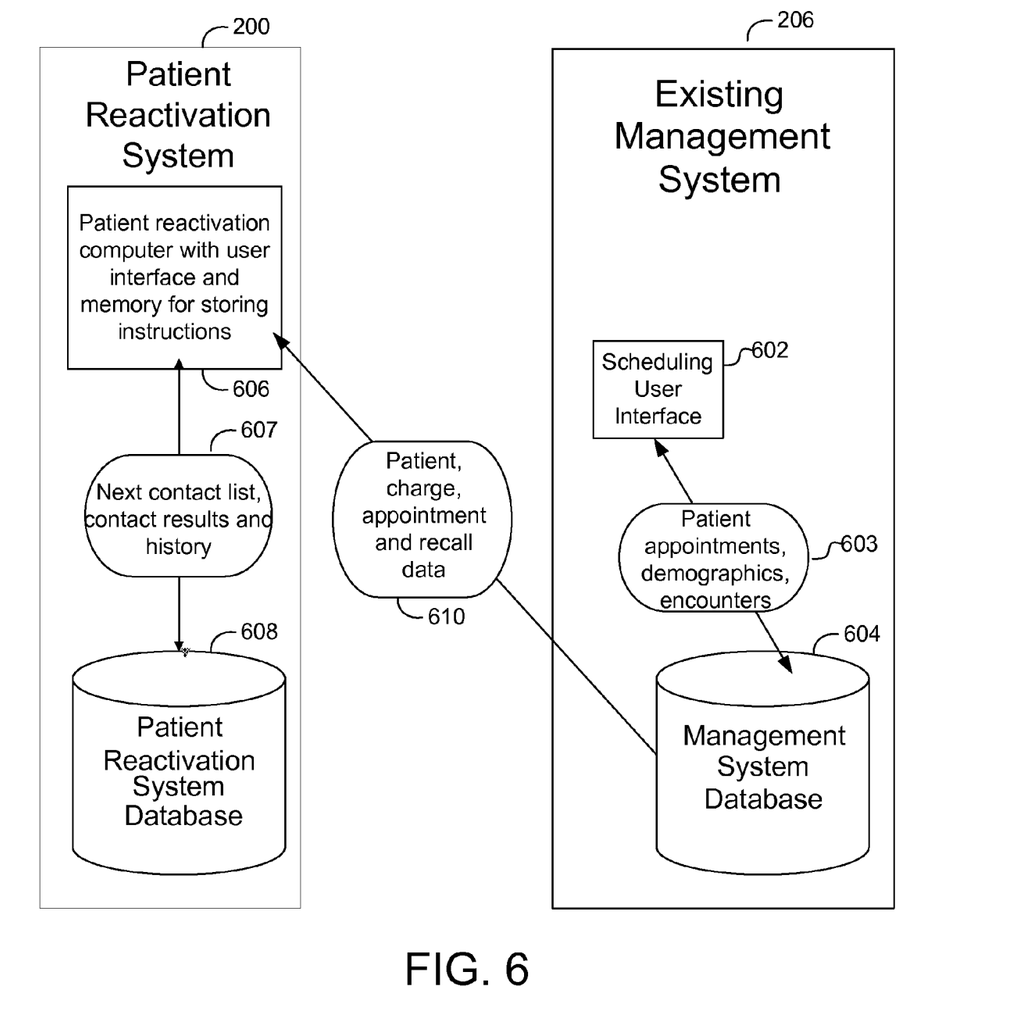
FIG. 6 shows schematically the hardware implementing the present invention.

FIG. 6 is a block diagram showing the patient reactivation system and an existing management system which can be used together to implement the invention. A patient reactivation system 200 includes a recall system user computer 606 with a user interface, including, for example, a video display by which a user can view information presented by the system about patients to be called, and a keyboard, mouse, or other device by which the user can enter data into a user computer on the system. In some embodiments, calls to patients may be automated, and made without human assistance. Patient reactivation system 200 also includes a patient reactivation system database 608 that stores lists of patients to contact and information about the patients necessary to make the contact. Patient reactivation system database 608 may be stored on user computer 606 or on a network storage location. The patient reactivation system 200 interfaces with the existing management system 206, which includes a scheduling user interface 602 and a management system database 604 that typically includes billing codes. As described above, the billing codes can be used to determine when additional visits are required.

The scheduling user interface 602 draws patient appointments 603 from the management system database 604, and writes new appointments 603 into the management system database 604. The patient reactivation system 200 determines, as described above, patients who should be contacted 610 and prompts one or more users to contact these patients. The contact results and history 607 are stored into the patient reactivation system database 608. The patient reactivation system 200 queries the patient reactivation system database 608 to avoid contacting patients redundantly or too frequently.

While the foregoing is a detailed description of the preferred embodiment of the invention, there are many alternative embodiments of the invention that would occur to those skilled in the art and that are within the scope of the present invention. For example, while the embodiment describes generating reminders for conditions that requires regular care, reminders can also be generated for conditions that require a single follow up visit. The term "medical" is used broadly herein to describe any health care related activity including, for example, dental, chiropractic, naturopathic, psychiatric, and psychological conditions or practices. The systems described herein can be used whenever follow up appointments are necessary. Accordingly, the present invention is to be determined by the following claims.

We claim as follows:

1. A computerized method for automatically identifying, using a computer running a medical or dental office practice management system and having a memory containing an office practice management system computer database and running a patient reactivation system and having a memory containing a patient reactivation system computer database, patients who are due for care so that those patients can be personally contacted by staff at a health care facility, comprising:

automatically querying a computerized medical or dental office practice management system database for standardized procedure or diagnostic codes in billing or other encounter data associated with past patient visits;

automatically identifying, using the standardized procedure or diagnostic codes, patients with medical conditions requiring regular care and storing data corresponding to the identified patients and their medical conditions in the patient reactivation system;

automatically determining a most recent date of treatment using billing or other encounter data from one of the computer databases;

automatically identifying patients who are due for care by comparing expected visit intervals for each condition with a time interval since the most recent date of treatment, and storing identifying data for the patients who are due for care in a contact list of the patient reactivation system;

automatically identifying patients who already have appointments or who will receive reminders to call for an appointment and automatically removing these patients from the contact list;

automatically identifying patients whose conditions have been resolved by comparing the standardized procedure or diagnostic codes with a set of procedures known to resolve each medical condition and automatically removing patients whose conditions have been resolved from the contact list;

displaying using a display on a computer screen patient identifying information to an operator, the patient information including at least an identified patient's name, telephone number, and reason why the identified patient is due for care;

contacting the identified patients by telephone call by the operator; and scheduling by the operator an appointment for healthcare while the patient is on the telephone.

2. The method of claim 1 in which scheduling an appointment includes transferring the telephone call to a scheduler.

3. The method of claim 1 further comprising displaying a screen that the operator can use to record results of the contact.

4. The method of claim 1 further comprising removing the patient from the contact list once the appointment has been scheduled.

5. A computerized method for automatically identifying, using a computer running a medical or dental office practice management system and having a memory containing an office practice management system computer database and running a patient reactivation system and having a memory containing a patient reactivation system computer database, patients who are due for care so that those patients can be personally contacted by staff at a health care facility, comprising:

automatically querying a computerized medical or dental office practice management system database for standardized procedure or diagnostic codes in billing or other encounter data associated with past patient visits;

automatically identifying, using the standardized billing or diagnostic codes, patients with medical conditions requiring regular care and storing data corresponding to the identified patients and their medical conditions in the patient reactivation system;

automatically determining a most recent date of treatment using billing or other encounter data from one of the computer databases;

automatically identifying patients who are due for care by comparing expected visit intervals for each condition with a time interval since the most recent date of treatment, and storing identifying data for the patients who are due for care in a contact list of the patient reactivation system;

automatically identifying patients who already have appointments or who will receive reminders to call for an appointment and automatically removing these patients from the contact list;

automatically identifying patients whose conditions have been resolved by comparing the standardized procedure or diagnostic codes with a set of procedures known to resolve each medical condition and automatically removing patients whose conditions have been resolved from the contact list;

displaying using a display on a computer screen patient identifying information to an operator, the patient information including at least the identified patient's name, telephone number, and reason why the patient is due for care;

attempting to contact the identified patient by the operator;

entering results of the attempted contact in a computer; and automatically determining from the entered results whether to schedule a follow-up contact.

6. The method of claim 5 further comprising displaying a screen that the operator can use to record the results of the attempted contact.

7. The method of claim 5 in which attempting to contact the patient includes receiving information indicating that the patient is not to be contacted and further comprising removing the patient from the contact list.

8. The method of claim 5 in which attempting to contact the patient includes receiving information indicating that the patient has a different telephone number and further comprising attempting to contact the patient using the new telephone number and recording the telephone number in the office database.

9. A computerized method for automatically identifying, using a computer running a medical practice management system having a computer database and a patient reactivation system having a computer database, and attempting to contact patients who are due for care, comprising:

automatically causing a computer to query a computerized medical or dental office practice management system database for standardized procedure or diagnostic codes in billing or other encounter data associated with past patient visits;

automatically causing a computer to identify, using the standardized procedure or diagnostic codes, patients with medical conditions requiring regular care and storing data corresponding to the identified patients and their medical conditions in the patient reactivation system;

automatically causing a computer to determine a most recent date of treatment using billing or other encounter data from the computer database;

automatically causing a computer to identify patients who are due for care by comparing expected visit intervals for each condition with a time interval since the most recent date of treatment, and storing identifying data for the patients who are due for care in a contact list of the patient reactivation system;

automatically causing a computer to identify patients who already have appointments or who are scheduled to receive reminders to call for an appointment and automatically removing these patients from the contact list;

automatically causing a computer to identify patients whose conditions have been resolved by comparing the standardized procedure or diagnostic codes with a set of procedures known to resolve each medical condition and automatically removing the patients whose conditions have been resolved from the contact list; and attempting to contact patients on the contact list by an operator.

10. The method according to claim 9, further comprising eliminating from the contact list: patients having specific insurance, patients over a given age, patients who have not been seen for a very long time, patients seen by specific doctors or at specific location, patients who have been discharged or are in collections, or patients who are deceased.

11. The method according to claim 9 in which attempting to contact patients on the contact list includes attempting to contact patients via a human caller using a telephone.

12. The method according to claim 9 in which attempting to contact patients on the contact list includes attempting to contact patients via an automated calling system.

13. The method according to claim 9, further comprising automatically generating recalls or mailing labels from the contact list to send patients written reminders to call for an appointment.

14. The method according to claim 9, further comprising automatically generating from the contact list email to patients requesting the patients to call for an appointment.

15. A non-transitory, computer-readable media having encoded thereon computer-readable instructions that, when executed by a computer, cause the computer to perform the steps of:

automatically querying a computerized medical or dental office practice management system database for standardized procedure or diagnostic codes in billing or other encounter data associated with past patient visits;

automatically identifying, using the standardized procedure or diagnostic codes, patients with medical conditions requiring regular care and storing data corresponding to the identified patients and their medical conditions in the patient reactivation system;

automatically determining a most recent date of treatment using billing or other encounter data from the database;

automatically identifying patients who are due for care by comparing expected visit intervals for each condition with a time interval since the most recent date of treatment, and storing identifying data for the patients who are due for care in a contact list of the patient reactivation system;

automatically identifying patients who already have appointments or who will receive a reminder to call for an appointment and automatically removing these patients from the contact list; and automatically identifying patients whose conditions have been resolved by comparing the standardized procedure or diagnostic codes with a set of procedures known to resolve each medical condition and automatically removing the patients whose conditions have been resolved from the contact list.

16. A computerized method for identifying patients who are due for care in an office that schedules appointments for the office using a computer running an office practice management system, comprising the steps of:
  causing a computer to identify patients with conditions requiring regular care using billing data from the practice management system;
  causing a computer to identify patients whose conditions have been resolved using billing data from the practice management system, wherein procedure codes from the billing data are compared to a set of procedure codes known to resolve each condition;
  causing a computer to determine a most recent date of treatment for unresolved conditions using billing data from the management system;
  causing a computer to identify a first group of patients who are due for care by comparing expected visit intervals for each condition with a time interval since last treatment, and storing identifying information of the identified patients from the first group of patients in a contact list; and
  causing a computer to identify a second group of patients whose conditions have been resolved, who already have appointments, or who will receive reminders to call for an appointment and removing identifying information of the identified patients from the second group of patients from the contact list.

17. The method according to claim 16, further comprising eliminating from the contact list patients based on one or more of the following criteria; patients having specific insurance, patients over a given age, patients who have not been seen for a very long time, patients seen by specific doctors or at specific location, patients who have been discharged or are in collections, or patients who are deceased.

18. The method according to claim 16, further comprising using the contact list to drive personal contact with patients via a human caller using a telephone.

19. The method according to claim 16, further comprising using the contact list to drive contact with patients via an automated calling system.

20. The method according to claim 16, further comprising using the contact list to automatically generate recalls or mailing labels to send patients written reminders to call for an appointment.

21. The method according to claim 16, further comprising using the contact list to automatically generate email to patients reminding them to call for an appointment.

22. An apparatus for identifying patients who are due for care in an office that schedules appointments for the office using a practice management system, the apparatus comprising a computer programmed with computer instructions for carrying out the following steps:
  automatically identifying, using standardized procedure or diagnostic codes in billing or other encounter data from a computerized medical practice management system, patients with conditions requiring regular care;
  automatically identifying patients whose conditions have been resolved using billing data from the practice management system, wherein procedure codes from the billing data are compared to a set of procedure codes known to resolve each condition;
  automatically determining a most recent date of treatment using billing or other encounter data from a database of the office management system;
  automatically identifying patients who are due for care by comparing expected visit intervals for each condition with a time interval since last treatment, and storing patient information related to those identified patients in a contact list;
  automatically identifying patients whose conditions have been resolved, who already have appointments, or who will receive reminders to call for an appointment and removing patient information related to those identified patients from the contact list.

23. A computerized method for automatically identifying, using a computer running a medical or dental office practice management system and having a memory containing an office practice management system computer database and running a patient reactivation system and having a memory containing a patient reactivation system computer database, patients who are due for care so that those patients can be personally contacted by staff at a health care facility, comprising:
  automatically querying diagnostic codes for past patient visits from billing or other encounter tables in a practice management system database associated with a medical or dental practice;
  automatically matching the diagnostic codes with a set of target codes for medical conditions requiring regular care and, for each matching diagnostic code, storing data in a patient-diagnosis table of a patient reactivation system database, the data at least identifying a patient and a diagnosis corresponding to the matching diagnostic code;
  automatically querying procedure codes and encounter dates from billing or other encounter tables in the practice management system for each entry in the patient-diagnosis table identifying a patient and a diagnosis corresponding to the matching diagnostic code to determine when each patient was last seen and what procedures were performed;
  automatically matching the procedure codes with a set of procedures known to resolve each medical condition and removing any entries in the patient-diagnosis table identifying a patient and a diagnosis corresponding to the matching diagnostic code for which a procedure has already been performed to resolve the diagnosis;
  automatically matching the procedure codes with a set of exam codes to determine a most recent exam date and storing the most recent exam date for each entry in the patient-diagnosis table identifying a patient and a diagnosis corresponding to the matching diagnostic code;
  automatically determining which entries in the patient-diagnosis table are overdue for care based on accepted standards of care or office policies and the most recent exam date for each entries in the patient-diagnosis table and storing in a contact list patient identifying data for each entry in the patient-diagnosis table identifying a patient and a diagnosis corresponding to the matching diagnostic code that is overdue for care;
  automatically querying the practice management system database do determine which patients in the contact list have appointments scheduled, pending recall notices, or an administrative flag and removing these patients from the contact list; and
  displaying the contact list to a user so that the user can contact one or more patients in the contact list to schedule an appointment for care.

* * * * *